(12) United States Patent
Reilly et al.

(10) Patent No.: US 8,162,903 B2
(45) Date of Patent: Apr. 24, 2012

(54) SYSTEM AND METHOD FOR PROPORTIONAL MIXING AND CONTINUOUS DELIVERY OF FLUIDS

(75) Inventors: David M. Reilly, Pittsburgh, PA (US); John F. Kalafut, Pittsburgh, PA (US); Ralph H. Schriver, Tarentum, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 12/848,570

(22) Filed: Aug. 2, 2010

(65) Prior Publication Data
US 2010/0298699 A1    Nov. 25, 2010

Related U.S. Application Data

(62) Division of application No. 11/928,021, filed on Oct. 30, 2007, now Pat. No. 7,766,883.

(51) Int. Cl.
*A61M 5/00* (2006.01)
(52) U.S. Cl. .......................... 604/248; 604/151; 604/246
(58) Field of Classification Search .............. 604/30–34, 604/65–66, 82, 85, 89, 537, 151, 246–249, 604/258; 600/431
See application file for complete search history.

(56) References Cited

U.S. PATENT DOCUMENTS

| | | | |
|---|---|---|---|
| 2,335,085 A | 11/1943 | Roberts | |
| 2,485,842 A | 10/1949 | Pennington | |
| 2,985,192 A | 5/1961 | Taylor et al. | |
| 3,057,350 A | 10/1962 | Cowley | |
| 3,157,201 A | 11/1964 | Littmann | |
| 3,411,534 A | 11/1968 | Rose | |
| 3,450,152 A | 6/1969 | Ouellette | |
| 3,834,372 A | 9/1974 | Turney | |
| 3,865,134 A | 2/1975 | Holcomb | |
| 3,918,490 A | 11/1975 | Goda | |
| 3,935,971 A | 2/1976 | Papoff et al. | |
| 3,957,082 A | 5/1976 | Fuson et al. | |
| 4,061,142 A | 12/1977 | Tuttle | |
| 4,071,039 A | 1/1978 | Goof | |
| 4,121,622 A | 10/1978 | Forberg | |
| 4,230,151 A | 10/1980 | Jonsson | |
| 4,259,985 A | 4/1981 | Bergmann | |
| 4,328,834 A | 5/1982 | Oates, Sr. et al. | |
| 4,468,914 A | 9/1984 | Pestes | |
| 4,484,599 A | 11/1984 | Hanover et al. | |
| 4,491,156 A | 1/1985 | Lee, II | |
| 4,637,817 A | 1/1987 | Archibald et al. | |
| 4,684,102 A | 8/1987 | Dykstra | |
| 4,819,637 A * | 4/1989 | Dormandy et al. ........... 606/195 |
| 4,821,996 A | 4/1989 | Bellotti et al. | |

(Continued)

*Primary Examiner* — Nicholas Lucchesi
*Assistant Examiner* — Melissa A Snyder
(74) *Attorney, Agent, or Firm* — Jill Denesvich

(57) ABSTRACT

A system and method for mixing and delivering fluids such as contrast media and saline is disclosed including at least two fluid sources, a pump, a joining fluid path connecting the at least two fluid sources to an inlet to the pump, and a valve device in the fluid path upstream of the pump. The valve device includes an actuator adapted to restrict flow in at least one of respective fluid lines connecting the at least two fluid sources to the pump inlet. A patient interface device may be associated with an outlet of the pump. The valve device actuator is generally adapted to restrict the flow in at least one of the respective fluid lines such that a positional change in valve device actuator position provides a change in fluid mixture ratio of the fluids from the at least two fluid sources to the pump inlet.

21 Claims, 10 Drawing Sheets

U.S. PATENT DOCUMENTS

| | | | |
|---|---|---|---|
| 4,946,434 A | 8/1990 | Plaisted et al. | |
| 4,967,797 A | 11/1990 | Manska | |
| 4,993,546 A | 2/1991 | Southard | |
| 5,084,031 A | 1/1992 | Todd et al. | |
| 5,097,840 A | 3/1992 | Wallace et al. | |
| 5,104,387 A | 4/1992 | Pokorney et al. | |
| 5,113,906 A | 5/1992 | Hogner | |
| 5,117,870 A | 6/1992 | Goodale et al. | |
| 5,135,026 A | 8/1992 | Manska | |
| 5,143,257 A | 9/1992 | Austin et al. | |
| 5,190,071 A | 3/1993 | Sule | |
| 5,205,322 A | 4/1993 | Merick et al. | |
| 5,207,642 A | 5/1993 | Orkin et al. | |
| 5,377,718 A | 1/1995 | Sand | |
| 5,450,847 A | 9/1995 | Kampfe et al. | |
| 5,460,609 A | 10/1995 | O'Donnell | |
| 5,462,251 A | 10/1995 | Kawabe | |
| 5,573,505 A | 11/1996 | Johnson et al. | |
| 5,573,515 A | 11/1996 | Wilson et al. | |
| 5,592,940 A | 1/1997 | Kampfe et al. | |
| 5,800,397 A | 9/1998 | Wilson et al. | |
| 5,806,519 A * | 9/1998 | Evans et al. | 600/431 |
| 5,817,068 A | 10/1998 | Urrutia | |
| 5,840,026 A | 11/1998 | Uber, III et al. | |
| 5,865,797 A | 2/1999 | Zeeman | |
| 5,885,216 A | 3/1999 | Evans, III et al. | |
| 5,901,745 A | 5/1999 | Buchtel | |
| 5,916,197 A | 6/1999 | Reilly et al. | |
| 6,079,691 A | 6/2000 | Dragone | |
| 6,197,000 B1 * | 3/2001 | Reilly et al. | 604/152 |
| 6,306,117 B1 | 10/2001 | Uber, III | |
| RE38,074 E | 4/2003 | Recinella et al. | |
| 6,575,930 B1 | 6/2003 | Trombley, III et al. | |
| 6,638,263 B1 | 10/2003 | Theeuwes et al. | |
| 6,648,017 B2 | 11/2003 | Lamas et al. | |
| 6,652,489 B2 | 11/2003 | Trocki et al. | |
| 6,676,104 B2 | 1/2004 | Tillander | |
| 6,682,044 B2 | 1/2004 | Miller | |
| 6,708,944 B2 | 3/2004 | Pfeil et al. | |
| 6,749,090 B2 | 6/2004 | Bailey | |
| 6,857,617 B2 | 2/2005 | Forberg | |
| 6,871,660 B2 | 3/2005 | Hampsch | |
| 6,892,996 B2 | 5/2005 | Starchevich | |
| 6,901,283 B2 | 5/2005 | Evans, III et al. | |
| 6,918,893 B2 | 7/2005 | Houde et al. | |
| 6,929,235 B1 | 8/2005 | Height et al. | |
| 6,929,236 B1 | 8/2005 | Height et al. | |
| 6,953,450 B2 | 10/2005 | Baldwin et al. | |
| 6,953,453 B2 | 10/2005 | Recinella et al. | |
| 6,958,053 B1 | 10/2005 | Reilly | |
| 7,047,058 B1 | 5/2006 | Dvorsky et al. | |
| 7,060,049 B2 | 6/2006 | Trombley, III et al. | |
| 7,094,216 B2 | 8/2006 | Trombley, III et al. | |
| 2002/0088954 A1 | 7/2002 | Miller | |
| 2002/0130283 A1 | 9/2002 | Starchevich | |
| 2003/0071233 A1 | 4/2003 | Stewart et al. | |
| 2004/0064041 A1 | 4/2004 | Lazzaro et al. | |
| 2004/0241023 A1 | 12/2004 | Pinkerton, III et al. | |
| 2005/0245883 A1 | 11/2005 | Baldwin | |
| 2006/0108008 A1 | 5/2006 | Guala | |
| 2006/0155248 A1 | 7/2006 | Hashimoto et al. | |
| 2006/0167415 A1 | 7/2006 | Nemoto | |
| 2007/0060874 A1 | 3/2007 | Nesbitt et al. | |
| 2007/0204612 A1 | 9/2007 | Klimowicz | |

* cited by examiner

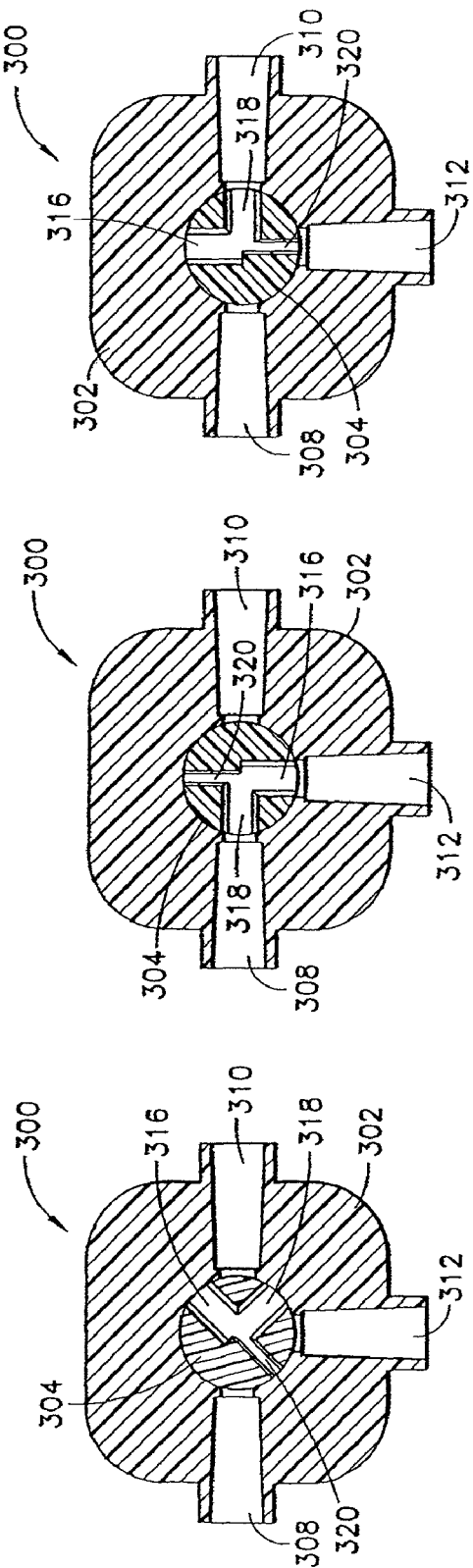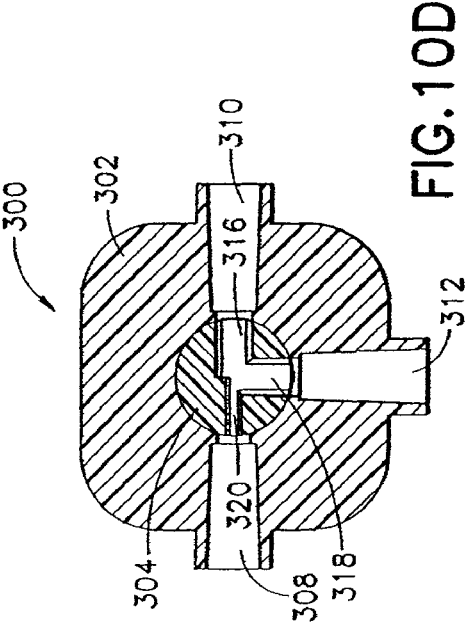

SYSTEM AND METHOD FOR PROPORTIONAL MIXING AND CONTINUOUS DELIVERY OF FLUIDS

CROSS-REFERENCE TO RELATED APPLICATION

This application is a division of application Ser. No. 11/928,021, filed on Oct. 30, 2007, the contents of which are incorporated herein by reference.

BACKGROUND OF THE INVENTION

1. Field of the Invention

The embodiments of the invention disclosed herein relate generally to the field of diagnostic and therapeutic medical procedures involving the intravenous infusion of fluids such as contrast-enhanced radiographic imaging as an example and, more particularly, to a system capable of controlled proportional mixing and delivery of fluid mixtures to a patient. In one specific application, contrast media may be proportionally mixed with another fluid such as saline for continuous delivery to a patient undergoing a medical radiographic imaging procedure.

2. Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media (often referred to simply as "contrast"), have been developed for use in procedures such as angiography, computed tomography ("CT"), ultrasound, and NMR/MRI. In general, these powered injectors are designed to deliver a preset amount of contrast at a preset flow rate.

Angiography is an example of a radiographic imaging procedure wherein a powered injector may be used. Angiography is used in the detection and treatment of abnormalities or restrictions in blood vessels. In an angiographic procedure, a radiographic image of a vascular structure is obtained through the use of a radiographic contrast medium which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical contrast-enhanced radiographic imaging procedure such as angiography, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual system controls the syringe and each of the valves to draw saline or contrast into the syringe and to inject the contrast or saline into the patient through the catheter connection.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector except to start or stop the injection. A change in flow rate in such systems occurs by stopping the machine and resetting the injection parameters. Automation of contrast-enhanced imaging procedures using powered injectors is discussed, for example, in U.S. Pat. Nos. 5,460,609; 5,573,515; and 5,800,397.

It is often desirable to deliver a mixture of contrast and a diluent such as saline to the patient undergoing the radiographic imaging procedure. Depending on a patient's particular physical characteristics, age, and the tissue to be imaged, the desirable concentration of contrast media varies. Medical practitioners can purchase pre-mixed solutions of contrast media in various discrete concentrations and this is a common practice in the medical field. Presently, contrast media is provided in sterilized glass bottles ranging in size from 20 ml to 200 ml. Plastic packages are also available. Presently used contrast media containers are single use which means that once a container is opened its contents must all be used for one patient and any residual unused contrast and the bottle must be discarded. As a result, a medical facility must purchase and stock many concentrations in multiple container sizes to provide the right amount of the right contrast concentration for a specific procedure while minimizing wastage of contrast remaining in any opened containers. This multitude of sizes and concentrations increases costs throughout the contrast supply chain. Contrast manufacturers are required to make many batches with various concentrations and package each in differently sized containers. The manufactures must have inventories of each concentration/container size on hand to quickly meet their customers' requests. Each concentration level and container size also entails an added regulatory burden.

In the end-use medical facility environment, there are additional costs due to the efforts required to purchase and stock various concentration/container sizes. Bulk storage space is required for stocking and cabinets are required in each procedure room. Moreover, labor and time are required to make sure the correct numbers of each container are kept in each procedure room. Finally, the present system results in waste and/or less than optimal studies if this complicated logistics chain fails at any point.

Presently, most medical facilities utilize a standard protocol for a given set of indications. For instance, for a CT scan of the liver, the protocol may call for 130 ml of contrast injected at 3 ml/s. This protocol is used for a wide variety of patient weights and physical conditions. One goal of this standardization is to minimize errors. Another goal is to decrease the likelihood of having to repeat the procedure, with the accompanying additional radiation and contrast dose to the patient. However, there are costs associated with this method. Many patients may get more contrast than they need for an image to be diagnostic. Overdosing wastes contrast but there is no way with the present contrast supply and delivery system to remedy this without stocking many more sizes of containers and being more judicious in the filling of injection syringes. Other patients may have studies that are less than optimal as they do not receive enough contrast and there is a much greater chance of having to repeat the procedure.

In angiography, there are no set protocols to the same extent as in CT because patient size determines vessel size which in turn determines the volume and flow rate required. This means that a fixed amount of contrast cannot be prepared ahead of time with any confidence that more will not be needed during the procedure or that a significant amount will not remain and be wasted at the end of the procedure. To avoid delays during an angiography procedure, the medical practitioner typically loads more contrast than the average amount to be used with the realization that some contrast is likely to be wasted.

A further result of the foregoing system is the accumulation of a significant amount of hazardous medical waste at the conclusion of the procedure. To save contrast, several small glass bottles may be opened per patient, one or more plastic syringes may be used, and various tubing arrangements may be used. Each of these items has an associated cost to purchase the item and an associated cost to properly dispose of the item.

Solutions have been proposed to overcome the foregoing problems associated with the use of a multiplicity of concentrations and container sizes and, further, to allow for more individualized contrast mixtures to be produced to meet individual patient requirements. For example, U.S. Pat. Nos. 5,592,940 and 5,450,847 to Kampfe et al. disclose a mixing system that allows for mixing contrast medium and saline "on site" at a medical facility. More particularly, the Kampfe et al. patents disclose an exemplary mixing system that involves withdrawing or removing predetermined amounts of contrast medium and a diluent (e.g., saline) from respective vessels and mixing these fluids in a mixing chamber and then delivering the mixed fluid to a suitable receiving container, such as a vial, bag, or syringe which is used to deliver the mixed fluid to a patient. Other contrast-diluent mixing systems are known from U.S. Pat. Nos. 6,901,283 to Evans, III et al. and 5,840,026 to Uber, III. et al., the disclosures of which are incorporated herein by reference. U.S. Pat. No. 7,060,049 to Trombley, III et al. discloses a system for injecting a multicomponent enhancement medium into a patient that incorporates an agitating mechanism to maintain the medium in a mixed state for injection and this patent is also incorporated herein by reference. Within the representative "mixing" systems disclosed in the foregoing patents, simple mechanical mixing devices are used to mix the respective fluids. For example, in the systems disclosed by Evans, III et al. and Uber, III et al., the fluids to be mixed are joined together as they flow through a static mixer that contains helical vanes. In the Kampfe et al. patents, a bulk mechanical mixer is used to mix two sequential flows. In each of these cases, fluid mixture proportions are determined by controlled metering valves or other devices (e.g., peristaltic pumps) in the flow path.

Other devices are known for use in fluid delivery systems having medical applications to mix and dispense a mixed fluid, for example, in preset and "fixed" concentration ratios. For example, a selector valve such as that disclosed in U.S. Pat. No. 3,957,082 to Fuson et al. is known to allow an operator to "dial-in" a selected fluid choice or mixture of fluids in a preset or predefined ratio. The Fuson et al. patent allows for the choice of a first fluid such as a drug, a second fluid such as saline, or preset "fixed" mixture ratio of the two fluids (e.g., a 50%-50% mixture) for delivery to a patient. U.S. Pat. No. 6,918,893 to Houde et al. discloses a selector valve having specific application in the delivery of contrast and saline in contrast-enhanced radiographic imaging procedures but this selector valve does not have the ability to dial in a desired mixture ratio of two fluids. The disclosure of U.S. Pat. No. 3,957,082 is incorporated herein for the selector valve teaching of this disclosure.

Double or dual pinch valves are also known for use in fluid handling systems to accomplish one or more of: alternating the flow of two fluids, blocking flow of the two fluids, or permitting simultaneous flow of the two fluids in a fluid path as disclosed in U.S. Pat. Nos. 2,985,192 (Taylor et al.); 3,411, 534 (Rose); 3,918,490 (Goda); 4,071,039 (Goof); 4,259,985 (Bergmann); and 4,484,599 (Hanover et al.). U.S. Pat. No. 6,871,660 to Hampsch discloses a solenoid operated double or dual pinch valve to provide alternating flow capability in a devices used in medical and pharmaceutical laboratory research. The various double or dual pinch valves disclosed in the foregoing patents, as indicated, have the ability to control the flow of the respective fluids through two channels by pinching none, one, or both of the channels through the pinch valve. Accordingly, these pinch valves allow for one channel to be completely open and the other to be completely closed so as to allow only one fluid to pass through the pinch valve, allow for both channels to completely open, or completely block both channels. As a result, these pinch valves provide no ability to mix or control the proportional mixing of two or more fluids in any desired proportion as provided in the embodiments disclosed herein in this disclosure. Such ability to mix or, more clearly, control the proportional mixing of two fluids has been attempted by varying the respective speeds at which two respective pump devices deliver fluids to a mixing fluid path, such as disclosed in U.S. Pat. No. 3,935,971 to Papoff et al., but such a system is in practice difficult to control as it involves regulating precisely motor speed of the motors driving the respective pump devices. As a result, such controlled, dual pump systems do not present a very accurate proportioned mixture to the output or delivery conduit. The foregoing shortcomings are overcome by the various embodiments described herein.

SUMMARY OF THE INVENTION

In one embodiment, a system for mixing and delivering fluids such as contrast media and a diluent such as saline is disclosed comprising at least two fluid sources, a pump, a joining fluid path connecting the at least two fluid sources to an inlet to the pump, and a valve device in the fluid path upstream of the pump. The valve device comprises an actuator adapted to restrict flow in at least one of respective fluid lines connecting the at least two fluid sources to the pump inlet. A controller may be operatively associated with the valve device for controlling positional movement of the valve device actuator. A patient interface device, such as a catheter as an example, may be associated with an outlet of the pump. The valve device actuator is generally adapted to restrict the flow in at least one of the respective fluid lines such that an incremental positional change in valve device actuator position provides a substantially linear change in fluid mixture ratio of the fluids from the at least two fluid sources to the pump inlet.

The fluids may comprise at least contrast media and a diluent such as saline. The valve device actuator may be adapted to simultaneously at least partially restrict flow in each of the respective fluid lines. In one embodiment, the pump comprises a positive displacement pump, for example, a multi-chamber piston pump. In another embodiment, the pump comprises a peristaltic pump. The respective fluid lines may have different diameters. The respective fluid lines may comprise compressible tubing, and the valve device may comprise a pinch valve and the valve device actuator may comprise a pinch block adapted to restrict flow in at least one of the respective fluid lines via compression of the compressible tubing. Movement of the pinch block may be effected by a servomotor. The respective fluid lines may be joined via a branch connector having an outlet in fluid connection with the pump inlet. A flow meter may be associated with at least one of the respective fluid lines. The controller may effect positional change of the valve device actuator at least in part based on feedback from the flow meter.

Another aspect disclosed herein relates to a method for mixing and delivering fluids such as contrast media and a diluent such as saline to a patient. Such a method generally includes providing a joining fluid path connecting at least two fluid sources to an inlet to a pump, providing a valve device including a valve device actuator in the fluid path upstream of the pump, and restricting the flow in at least one of the respective fluid lines with the valve device actuator. The valve device actuator is generally adapted to restrict flow in at least one of respective fluid lines connecting the at least two fluid sources to the pump inlet. The flow is restricted in at least one of the respective fluid lines by the valve device actuator such that an incremental positional change in valve device actuator position provides a substantially linear change in fluid mixture ratio of the fluids from the at least two fluid sources to the pump inlet.

The fluids may again comprise contrast media and a diluent such as saline. Another feature of the method relates to associating a patient interface device, such as a catheter as an example, with an outlet of the pump. In one alternative, the valve device actuator simultaneously at least partially restricts flow in each of the respective fluid lines. A further feature of the method relates to associating a flow meter with at least one of the respective fluid lines. In one embodiment, the pump comprises a positive displacement pump. In another embodiment, the pump comprises a peristaltic pump. The respective fluid lines may have different diameters. As noted hereinabove, the respective fluid lines may comprise compressible tubing, and the method may further comprise at least partially compressing the compressible tubing of at least one of the respective fluid lines with the valve device actuator to restrict flow. In one embodiment, the valve device may comprise a pinch valve and the valve device actuator may comprise a pinch block adapted to restrict flow in at least one of the respective fluid lines via compression of the compressible tubing. A flow meter may be associated with at least one of the respective fluid lines and the method may further comprise a controller effecting positional change of the valve device actuator at least in part based on feedback from the flow meter.

Further details and advantages will become clear upon reading the following detailed description in conjunction with the accompanying drawing figures, wherein like parts are identified with like reference numerals throughout.

BRIEF DESCRIPTION OF THE DRAWINGS

FIGS. 10A-10E are respective cross-sectional views of the mixing stopcock valve of FIGS. 8-9 showing various operational states of the valve.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices illustrated in the accompanying drawing figures and described herein are simply exemplary and should not be considered as limiting.

Figure 1:
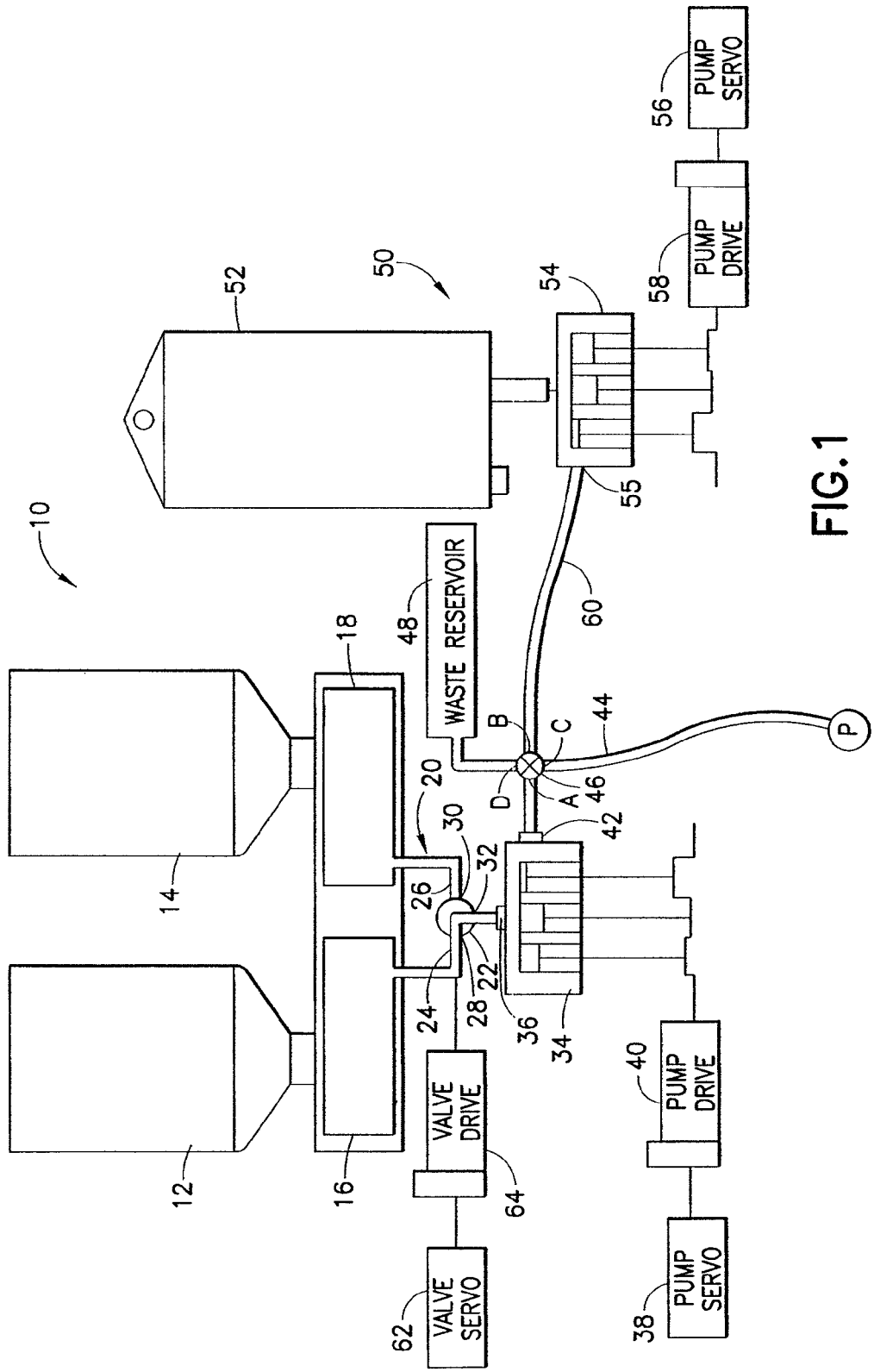
FIG. 1 is a schematic view of a fluid delivery system wherein two fluids may be delivered through use of two pumps to a patient.

FIG. 1 illustrates an exemplary system 10 for delivering contrast media and a diluent, such as saline, to a patient in a sequential or simultaneous manner via the use of two pump platforms. While system 10 is described in the context of the delivery of contrast and saline, for example, to a patient, system 10 may be applicable for situations where it is desired to supply any two fluids to a patient intravenously. It will be further appreciated that system 10 may be readily expanded to deliver multi-fluids (e.g., more than two fluids) to a patient. In the illustrated and non-limiting example, contrast media of similar or different concentrations is contained in respective conventional containers 12, 14. Respective and optional delivery reservoirs 16, 18 are associated with contrast containers 12, 14. A contrast fluid path 20 joins or connects the respective contrast reservoirs 16, 18 to a manual or automatic selector valve 22 provided in contrast fluid path 20. Contrast fluid path 20 includes a first input line 24 and a second input line 26 connecting the respective reservoirs 16, 18 to first and second input ports 28, 30, respectively, to selector valve 22. An output port 32 of selector valve 22 is associated with or connected to a first pump 34 and, in particular, an inlet port 36 of first pump 34. First pump 34 may be of conventional design such as the positive displacement, multi-piston pump disclosed in U.S. Pat. No. 6,197,000 to Reilly et al. incorporated herein by reference. Motive forces to operate first pump 34 are provided by a pump servomotor 38 and pump drive 40. Outlet port 42 of first pump 34 is associated or connected to a patient P via patient fluid path 44 and the output from first pump 34 to patient P is controlled by interposing a stopcock 46 in patient fluid path 44. Stopcock 46 has an input port associated with the outlet port 42 of first pump 34 and further includes an outlet port associated with a waste reservoir 48. Other features of stopcock 46 are described hereinafter.

Another portion of system 10 is a diluent delivery portion 50 wherein a diluent such as saline is provided in a conventional IV bag type container 52. A second pump 54, which is typically identical to first pump 34, has an outlet 55 connected to the patient fluid path 44 via stopcock 46 to provide saline solution to patient P and/or saline flush to fluid path 44. Second pump 54 is provided with its own pump servomotor 56 and pump drive 58. Diluent container 52 is connected via a diluent fluid path 60 to a second input port on stopcock 46 so as to provide diluent supply and flush to patient fluid path 44. As shown in FIG. 1, stopcock 46 has a first input port A associated outlet port 42 of pump 46, a second input port B associated with associated outlet port 55 of second pump 54, a first outlet port C associated with patient fluid path 44, and a second outlet port D associated with waste reservoir 48. Selector valve 22 may be automatically or remotely operated via control of a valve servomotor 62 and associated valve drive 64 and may be, for example, an automated stopcock. If desired, stopcock 46 may be automated in a similar manner to selector valve 22. A controller (not shown) may be provided to automate operation of system 10 via control of pump servomotors 38, 56 and valve servomotor 62.

In operation, selector valve 22 may be operated to select the contents of one of the two provided contrast-containers 12, 14 which allows pump 34 to extract the selected contrast medium via contrast fluid path 20 and selector valve 22 and deliver the selected contrast medium to patient fluid path 44 via stopcock 46. Saline may be delivered to patient fluid path 44 via stopcock 46 by operation of second pump 54 and diluent fluid path 60. Pumps 34, 54 may be alternately operated to sequentially supply selected contrast medium and saline to patient fluid path 44. Alternatively, both pumps 34, 54 may be operated simultaneously, with mixing of the selected contrast medium and saline occurring in the patient fluid path 44 and/or in stopcock 46. Stopcock 46 is desirably configured to permit at least partial simultaneous fluid communication to be present between pump outlet 42 of first pump 34 and pump outlet 55 of second pump 54 with patient fluid path 44 to permit simultaneous delivery of both contrast medium and saline to patient fluid path 44.

Typically, mixing of the selected contrast media and saline to achieve any desired proportional mixture of these fluids is accomplished by controlling the flow rate delivered by the respective pumps 34, 54. However, this is also a disadvantage with system 10 as two separate pumps 34, 54 must be operated and, further, their operations coordinated to deliver a desired, proportioned mixture of contrast and saline to patient fluid path 44. This arrangement is similar to that disclosed in U.S. Pat. No. 3,935,971 to Papoff et al. discussed previously, wherein the operating speeds of two peristaltic pumps must be controlled and coordinated to obtain a desired proportional mixture of two fluids. In system 10, similar control of pumps 34, 54 is necessary to obtain a desired mixture ratio or proportional mixture of contrast and saline. The pump control aspects of U.S. Pat. No. 3,935,971 to Papoff et al. applicable to the control of pumps 34, 54 are incorporated herein by reference.

Mixing of the selected contrast medium and saline may also be accomplished with use of a "mixing" stopcock valve for stopcock 46, such as disclosed in U.S. Pat. No. 3,957,082 to Fuson et al., incorporated by reference previously (but as a two-fluid version of this valve), rather than by operational control of pumps 34, 54. However, a preferred mixing stopcock valve 300 particularly suitable for this application is discussed herein in connection with FIGS. 8-10 which accounts for upstream pressure and/or viscosity differences between contrast medium and saline which is not a feature or consideration of the Fuson et al. mixing stopcock. It is noted that selector valve 22 may also be a mixing stopcock valve as disclosed in the Fuson et al. patent (but as a two-fluid version of this valve) if it is desired to mix the contents of contrast containers 12, 14 in a preset or "fixed" proportional mixture prior to delivering this contrast mixture to first pump 34. However, again, such a known mixing stopcock valve as disclosed by Fuson et al. does not account for upstream pressure and/or viscosity differences which may be present between the contrast media present in contrast containers 12, 14 as does the mixing stopcock valve 300 illustrated in FIGS. 8-10 and discussed herein. Use of mixing stopcock valve 300 in system 10 permits pumps 34, 54 to operate at the same or substantially the same speeds, which proportional mixing being accomplished by valve 300, as described herein.

Figure 2:
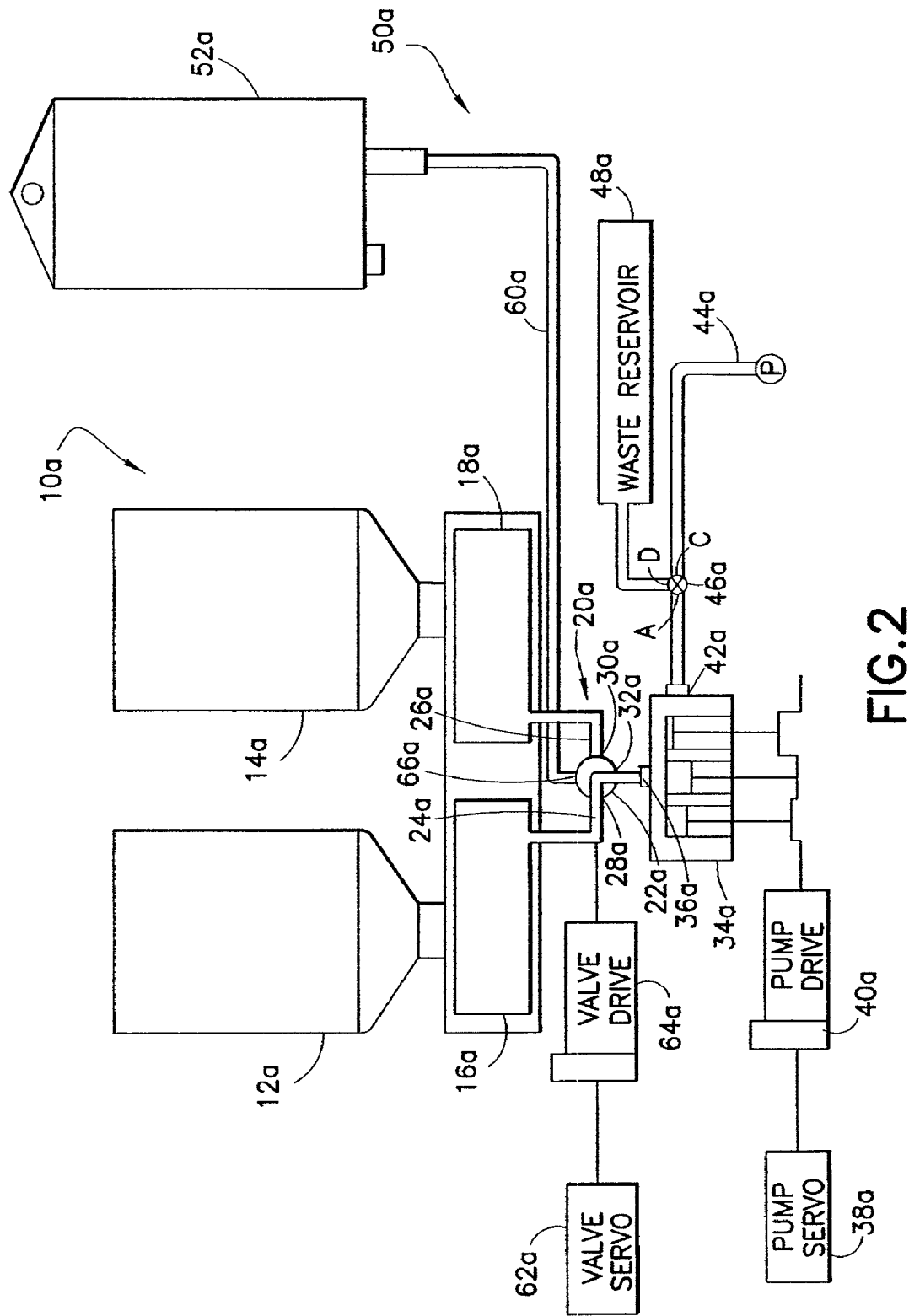
FIG. 2 is a schematic view of a fluid delivery system wherein multi-fluids may be delivered to a patient through use of a single pump.

FIG. 2 illustrates a variation of system 10 referred to as system 10a which eliminates second pump 54 by directly connecting diluent container 52a via diluent fluid path 60a to a third input port 66a of selector valve 22a. Accordingly, contrast media from contrast containers 12a, 14a and saline from diluent container 52a are each connected through single selector valve 22a so that any one of these three fluids may be provided via pump 34a to patient fluid path 44a. However, in this specific configuration, typically only one fluid at a time may be provided to patient P via patient fluid path 44a providing only the ability to provide sequential flow of the fluids to patient P. As a result, modified system 10a lacks the ability to mix contrast media and diluent such as saline, proportionally or otherwise, and deliver a mixture of contrast and diluent to patient P without modification to selector valve 22a. While it may be possible to replace selector valve 22a with the mixing stopcock valve disclosed in U.S. Pat. No. 3,957,082 to Fuson et al. which allows an operator to "dial-in" a selected fluid choice or a preset proportional mixture of fluids (e.g., a 50%-50% mixture), the Fuson et al. stopcock valve does not account for upstream pressure and/or viscosity differences, as noted previously, which may be present between the fluids entering such a stopcock as does mixing stopcock valve 300 described herein in connection with FIGS. 8-10. In general, the conventional mixing stopcock valve disclosed by Fuson et al. is limited in application to permitting full fluid flow from a first fluid sources, full fluid flow from a second fluid source, or at most a few preset or "fixed" proportional mixture settings for the two fluids to be delivered to a patient and, hence, does not permit a full range of fluid mixture ratios or proportions to be delivered to a patient as provided by the system 100 discussed herein in connection with FIGS. 3-7. The operational control of pumps 34, 54 in system 10 discussed previously may provide a fuller range of fluid mixture ratios or proportions to be delivered to a patient but respective operational control of pumps 34, 54 is difficult in practice to achieve with accuracy particularly when the two fluids have significantly different viscosities as is the case with contrast media and saline. It will be clear that, if desired, additional fluid sources may be provided in system 10a with each having an additional input line to selector valve 22a.

Figure 3:
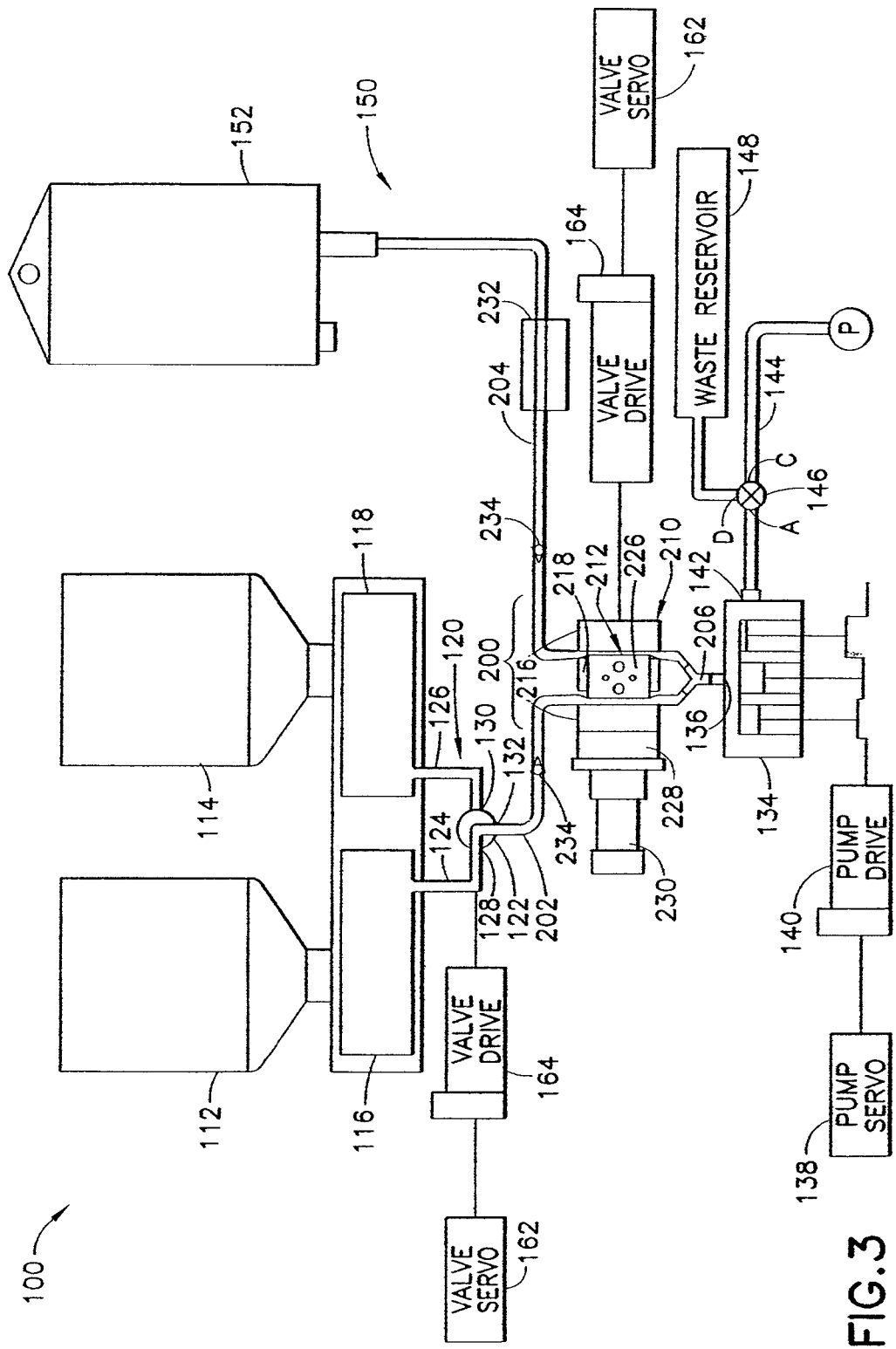
FIG. 3 is a schematic view of an embodiment of a system capable of controlled proportional mixing of fluids and continuous or intermittent delivery thereof to a patient.
Figure 4:
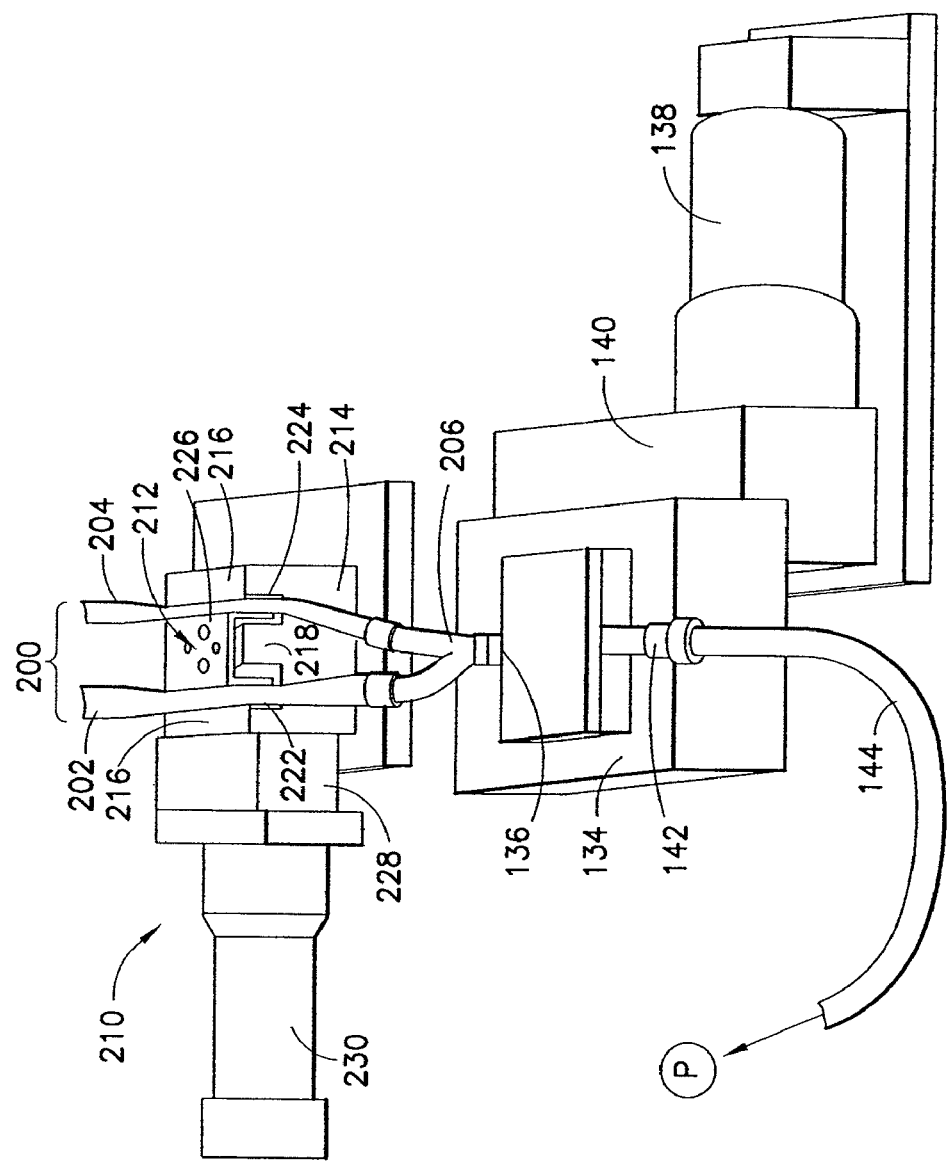
FIG. 4 is a perspective view of a portion of the system shown in FIG. 3 showing a pump and a valve device of the system.

FIG. 3 is a schematic representation of an embodiment of a system 100 capable of controlled proportional mixing of fluids and further capable of intermittent or continuous delivery of a proportional mixed fluid to a patient. In one example, the fluids may be contrast media and saline which may be proportionally mixed in any desired mixture ratio and delivered either intermittently or continuously to a patient undergoing medical radiographic imaging procedure. System 100 is described for exemplary purposes in the context of contrast media and saline and the controlled proportional mixing and delivery thereof to a patient P to explain the features of the invention. However, this specific application or explanation should not be considered as precluding the use of system 100 in other situations. Generally, system 100 is suitable for use in any situation where it is desired to mix two (or more) fluids in a controlled proportional manner and deliver such as a mixed fluid intermittently or continuously to a patient undergoing a medical procedure involving intravenous fluid infusion, such as the proportional mixing of a drug with a diluent such as saline as an example. A full range of proportional mixtures between two (or more) fluids may be obtained as outputs to the patient P as described herein. Moreover, it is explicitly noted that the principle of operation of system 100 may be expanded to multi-fluids (e.g., three or more) if desired. System 100 has similar architecture to systems 10, 10a discussed previously with certain alterations and additions as described herein. Accordingly, in view of the foregoing, it is expressly noted that system 100 is not limited to just two fluids and is specifically not limited to contrast and saline as fluids which may be handled by system 100.

In system 100, contrast media of similar or different concentrations is contained in respective conventional containers 112, 114. Respective and optional contrast reservoirs 116, 118 are associated with contrast containers 112, 114. A contrast fluid path 120 joins or connects the respective reservoirs 116, 118 to a manual or, desirably, automatic selector valve 122 provided in contrast fluid path 120. Contrast fluid path 120 includes a first input line 124 and a second input line 126 connecting the respective contrast reservoirs 116, 118 to first and second input ports 128, 130 to selector valve 122. An output port 132 of selector valve 122 is associated with or connected to a pump 134 and, in particular, an inlet port 136 of pump 134 via a joining fluid path 200 which is associated with an intervening valve device 210. The details of joining fluid path 200 and valve device 210 are described hereinafter.

Pump 134 may be of conventional design such as the positive displacement, multi-piston pump disclosed in U.S. Pat. No. 6,197,000 to Reilly et al., previously incorporated herein by reference. Motive forces to operate pump 134 are provided by a pump servomotor 138 and pump drive 140. An outlet port 142 of pump 134 is associated or connected to a patient P via patient fluid path 144 and the output from pump 134 to patient P is controlled by interposing a stopcock 146 in patient fluid path 144. Stopcock 146 has an input port associated with the outlet port 142 of pump 134 and further includes an outlet port associated with a waste reservoir 148. Peristaltic pumps may also be used as in place of the positive displacement pump disclosed by Reilly et al. Peristaltic pumps are well-known in the medical filed for delivery fluids to patients.

Another portion of system 100 is a diluent delivery portion 150 wherein a diluent such as saline is provided in a conventional IV bag type container 152. Diluent container 152 is connected via joining fluid path 200 to inlet port 136 of pump 134. Valve device 210 is operable to control the flow of contrast and saline in joining fluid path 200 to achieve desired proportional mixing of contrast and saline entering pump 134 via pump inlet 136. As shown in FIG. 3, stopcock 146 has a first input port A associated outlet port 142 of pump 136, and first and second outlet ports C, D associated with patient fluid path 144 and waste reservoir 148, respectively. Selector valve 122 may be automatically or remotely operated via control of a valve servomotor 162 and associated valve drive 164. If desired, stopcock 146 may be an automated stopcock, for example, and automated in a similar manner to selector valve 122. Selector valve 122 may also be a "mixing" stopcock valve as disclosed in the Fuson et al. patent described previously (but a two-fluid version of this valve), if it is desired to mix the contents of contrast containers 112, 114 in preset or "fixed" proportions or ratios prior to delivering this contrast mixture to joining fluid path 200. As noted previously, the Fuson et al. "mixing" stopcock valve does not account for upstream pressure and/or viscosity differences which may be present between the contrast media present in contrast containers 112, 114 as does mixing stopcock valve 300 discussed herein in connection with FIGS. 8-10.

Figure 5:
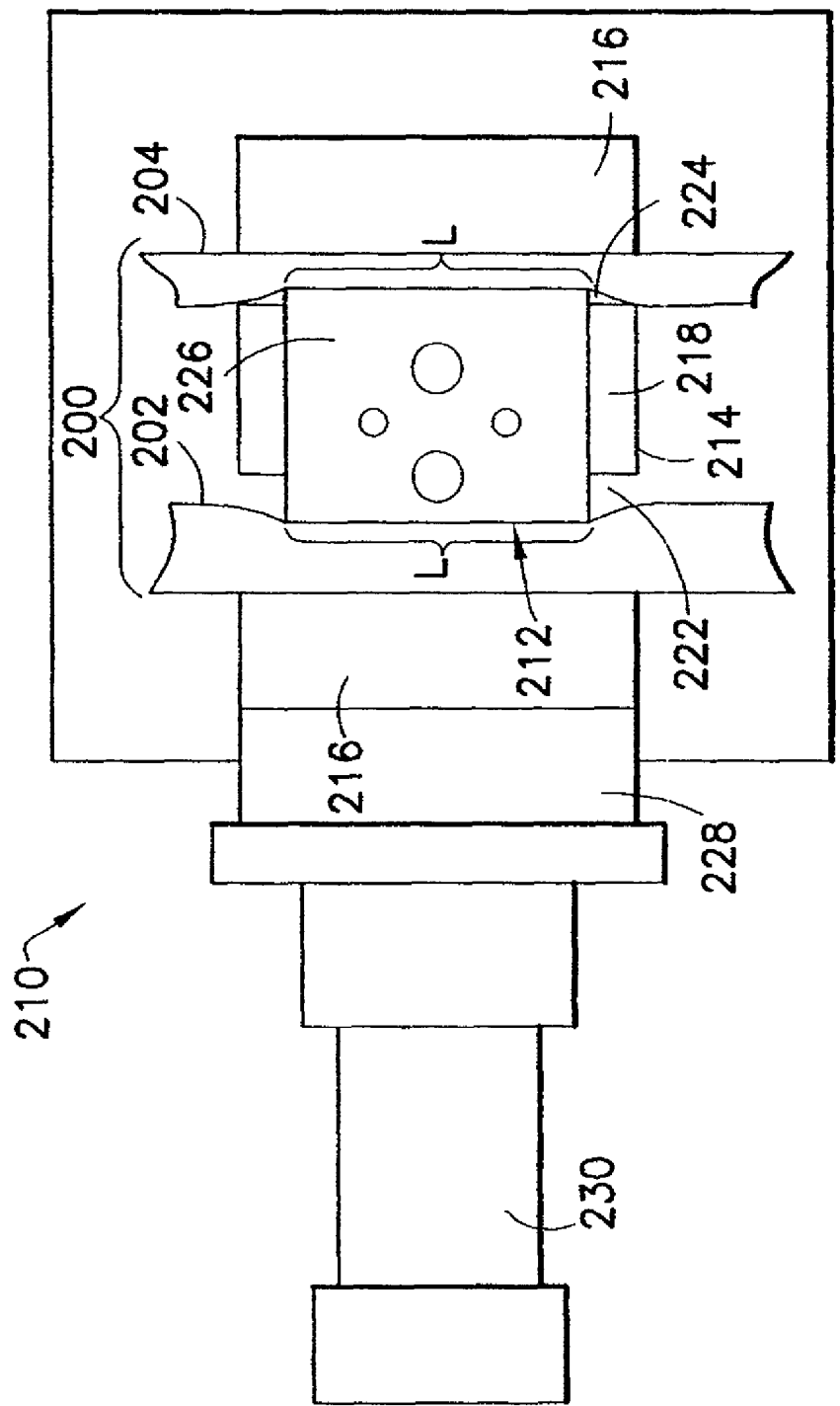
FIG. 5 is a plan view of the valve device provided in the system of FIGS. 3-4.

Referring further to FIG. 4-7, further details of system 100 including joining fluid path 200 and valve device 210 are shown. Joining fluid path 200 comprises a first fluid branch or line 202 to conduct selected contrast medium to the pump inlet 136 of pump 134 and a second fluid branch or line 204 to conduct diluent (typically saline) to the pump inlet 136 of pump 134. The first and second fluid lines 202, 204 are joined via a joining connector 206, such as a conventional T-connector or a conventional Y-connector as shown. Joining connector 206 is in fluid communication with pump inlet 136 to provide selected contrast medium and saline as a mixture to pump 134 which delivers this fluid mixture to patient fluid path 144 via stopcock 146. Desirably, first and second fluid lines 202, 204 are conventional medical tubing made of a flexible and resiliently compressible material, such as medical grade silicone tubing. As shown in FIG. 5, each of the first and second fluid lines 202, 204 comprises a portion or length L associated with valve device 210 so that valve device 210 is operable to act upon this length L of the first and second fluid lines 202, 204 to restrict fluid flow in one or both of the first and second fluid lines 202, 204.

Figure 6:
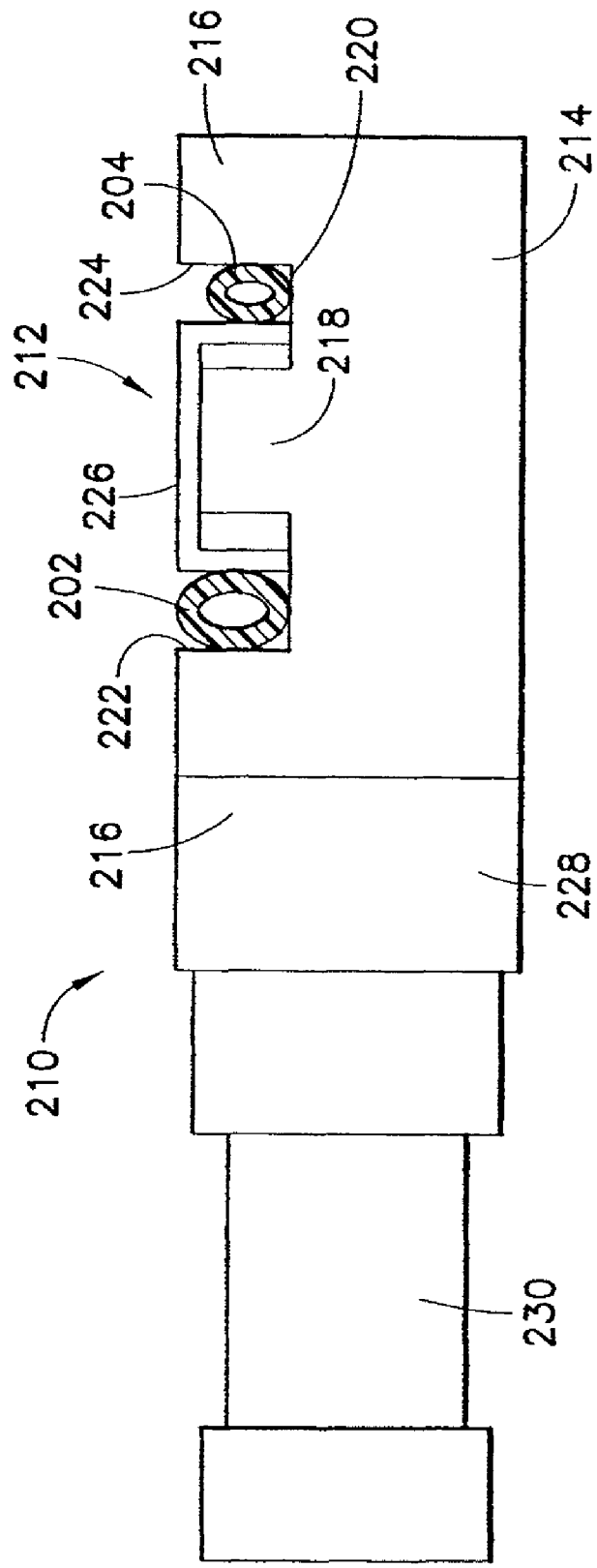
FIG. 6 is a front and partial cross-sectional view of the valve device of FIG. 5.

As best illustrated in FIG. 6, it will be apparent that first and second fluid lines 202, 204 may have different diameters with the second "diluent" fluid line 204 having a smaller diameter than the first "contrast" fluid line 202. This illustration is relevant for contrast media and saline as the fluids to be mixed in system 100 and should not be considered as limiting or exhaustive. The diameters of fluid lines 202, 204 may be set as necessary to achieve controlled proportional mixing of two fluids to deliver a desired mixture ratio of these fluids to pump 134, as described herein. In the case of contrast and saline, which have significantly different viscosities, diluent fluid line 204 is typically smaller in diameter than contrast fluid line 202 as saline has a lower viscosity than typical contrast media. However, in the case where system 100 is used to mix two fluids of similar viscosity and upstream head pressure, the diameters of fluid lines 202, 204 may be roughly or exactly equal. Generally, the fluid associated with fluid line 202 in system 100 has a higher viscosity than the fluid associated with fluid line 204 in system 100 and this generally translates into fluid line 202 having a larger diameter than fluid line 204 to achieve proportional mixing in a "linear" manner pursuant to the discussion herein.

In one embodiment, valve device 210 may be a dual pinch valve that includes a valve actuator 212 operably associated with the first and second fluid lines 202, 204 associated with valve device 220. In the illustrated configuration, valve device 210 comprises a base 214 having two laterally disposed, spaced apart, and upstanding sidewalls 216. The base 214 comprises an upstanding dividing portion 218 in an area 220 defined between sidewalls 216. Sidewalls 216 and dividing portion 218 define a pair of generally parallel channels 222, 224 which accommodate first and second fluid lines 202, 204, respectively. In particular, channels 222, 224 accommodate the length L of the first and second fluid lines 202, 204 which are to be operably engaged by valve actuator 212 as described herein. In one embodiment, valve actuator 212 comprises a pinch block 226 which is movable laterally or horizontally in area 220 to apply compressive forces to one or both of the first and second fluid lines 202, 204. Pinch block 226 is movable in a lateral, side-to-side manner in area 220 by a coupled drive mechanism 228 and servomotor 230. A feature of the configuration of valve device 210 relates to pinch block 226 being appropriately sized, configured, and positioned in area 220 such that both the first and second fluid lines 202, 204 are in a partial state of compression in channels 222, 224 and, thereby, provide flow restriction to the respective fluids passing through the first and second fluid lines 202, 204, namely contrast and saline. Such mutual compression of fluid lines 202, 204 aid in "linear" proportional mixing of contrast and saline during operation of system 100 as described herein. A flow meter 232 is associated with at least one of the fluid lines 202, 204, typically the second "saline" fluid line 204 to measure flow rate of saline to pump inlet 136 of pump 124. Moreover, check valves 234 may be provided in fluid lines 202, 204 to prevent backflow to contrast media containers 112, 114 and diluent container 152 during operation of system 100. A control device or controller 240 is provided in system 100 to control operation of the system 100. As such, controller 240 is electronically connected for two-way communication with at least pump servomotor 138 and pinch block servomotor 230 used to control movement pinch block 226, and desirably in two-way communication with flow meter 232 and selector valve servomotor 162, although flow meter 232 may be adapted just to provide saline flow rate information to controller 240.

In operation, system 100 in the exemplary embodiment outlined in the foregoing delivers a mixture of contrast and saline in any desired proportion or mixture ratio and, with appropriate control of pump 134, this proportional fluid mixture may be delivered to patient P continuously or intermittently as desired. Moreover, system 100 may be controlled such that for incremental or discrete changes in position of valve actuator 212, substantially linear fluid mixture ratio changes between contrast and saline are obtained at the pump inlet 136 which is then delivered by pump 134 via stopcock 146 to patient fluid path 144 and patient P. In system 100, flow rate of saline is determined or known as an input to controller 240 from flow meter 232 and total output flow from pump 134 is a known quantity as a positive-displacement type pump (e.g., operational feedback from pump servomotor 138). From these inputs to controller 240, the amount of contrast needed for a desired proportional mixture at pump inlet 136 may be calculated by controller 240. Controller 240 may then control positioning of pinch block 226 via pinch block servomotor 230 based on the feedback from flow meter 232 and pump servomotor 138. Since flow rate of contrast and saline in fluid lines 202, 204 relates to pressure drop in each line and this changes with viscosity of the respective fluids, differential diametrical sizing of fluid lines fluid lines 202, 204 may be used to provide a generally linear mixing ratio response with positional change of pinch block 226. In other words, controller 240 may continuously change lateral position of pinch block 226 based on inputs (feedback) from flow meter 232 and pump servomotor 138 to provide more or less compression to one or the other of contrast and saline fluid lines 202, 204 which are pre-selected in advance such that this changing compression results in a generally linear mixture ratio response change at pump inlet 136. Accordingly, this result is achieved by sizing fluid lines 202, 204 appropriately and feedback control of pinch block 226 in area 220 such that for each incremental or discrete change in horizontal, side-to-side position of pinch block 226 in area 220, one and, typically, both of the first and second fluid lines 202, 204 will undergo different degrees of compression (more or less) in channels 222, 224 and, therefore, restriction and as a result the concentration of contrast media entering pump inlet 136 changes by substantially a directly proportional or "linear" amount. This directly proportional or linear relationship between pinch block 226 position and contrast medium concentration is reflected in FIG. 7 illustrating a specific implementation or example of operation of system 100.

Figure 7:
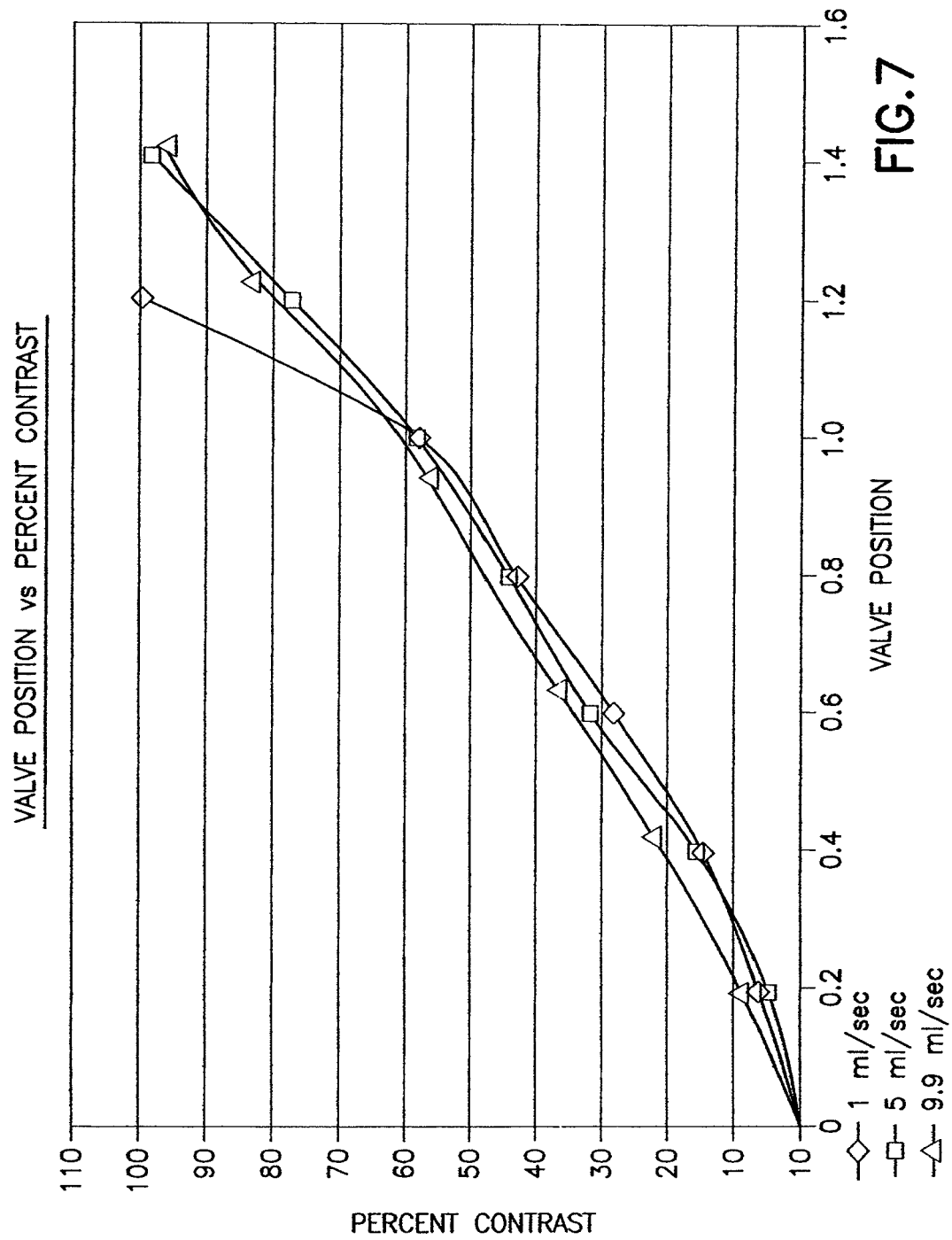
FIG. 7 is a graphical representation of contrast medium concentration as a function of position of the valve device of FIGS. 5-6.

In the specific and non-limiting example resulting in the graphical model shown in FIG. 7, first or contrast fluid line 202 may have a diameter of 0.187 in and second or saline fluid line 204 may have a diameter of 0.062 in. First and second fluid lines 202, 204 are disposed in respective channels 222, 224. Valve device actuator 212, namely, pinch block 226 is disposed in area 220 such that pinch block 226 at least partially compresses both fluid lines 202, 204 restricting fluid flow of contrast and saline therein, respectively. Flow rate of saline is determined or known from flow meter 232 and total output flow from pump 134 is a known quantity as described previously. As further described previously, change in lateral or side-to-side position of pinch block 226 is controlled by drive mechanism 228 and accompanying servomotor 230. A software algorithm is desirably provided in a control device or controller 240 to control with precision the movement of pinch block 226 in area 220. Such controlled movement of pinch block 226 controls with generally equal precision the amount of compression or restriction in one or both of fluid lines 202, 204. FIG. 7 illustrates that with appropriate relative sizing between fluid lines 202, 204 and feedback control of pinch block 226, incremental positional changes of pinch block 226 result in substantially directly proportional or linear changes in contrast concentration to pump inlet 136 of pump 134 over a range of fluid flows. Accordingly, if it is desired to adjust contrast concentration down or up, movement of pinch block 226 permits additional or less saline pass through valve device 210. For example, if additional saline is required to adjust the desired ratio, pinch block 226 is controlled in response to provide less restriction or compression of saline fluid line 204 while further restricting or compressing contrast fluid line 202. While the foregoing operation of system 100 was described in a manner indicating that both fluid lines 202, 204 are each in partial compression during operation of system 100, it will be clear to those skilled in the art that this need not always be the case and that the system 100 may be configured such that only one fluid line is compressed at a time during operation of system 100.

In the foregoing non-limiting example, the relationship between the change in position of pinch block 226 and the contrast medium concentration has been described as substantially linear. However, it should be noted that nonlinear relationships can be obtained by variations of system 100. For example, for some incremental changes in position of pinch block 226, the concentration of contrast medium may change exponentially or by some other nonlinear factor. For example, if the position changes by an amount x, the concentration may increase by an amount proportional to $x^n$. Such nonlinear relationships may be achieved depending upon several factors including the particular sizes and configurations of the components of system 100, fluid viscosities of the fluids involved, upstream pressure differential, and flow rates utilized.

While the foregoing system 100 and its operation was described with reference to two specific fluids, namely, contrast and saline, this should not be considered as limiting as noted previously. Additionally, system 100 may be expanded to accommodate additional fluids beyond just the two-fluid application discussed hereinabove. This may be accomplished, for example, by adding a third fluid source and an accompanying third flow path in joining flow path 200 passing through valve device 210 and configuring valve device 210 and, namely, valve actuator 212 to act upon this third or additional flow path. In such a situation, pinch block 226 may be sized and configured to include depending portions that can simultaneously compress or pinch two or more of the multi-flow flow paths. For example, in a three-fluid modification, an additional "middle" side wall 216 could be provided to operate on a "middle" flow path so that the modified pinch block 226 can compress it in addition to one of the other two paths. In this manner, two of the three flow paths may be restricted while the other is unrestricted. Alternatively, two separately controlled pinch blocks 226 may be used on respective sides of the "middle" flow path so that the pinching is independently performed by each pinch block 226, allowing the two pinch blocks to move in opposite directions. Moreover, while it was indicated in the foregoing that both fluid lines 202, 204 of joining flow path 200 are each typically at least partially compressed or restricted during operation of valve device 210 and valve actuator 212, fluid lines 202, 204 and valve device 210 and, namely, valve actuator 212 may be designed such that only one of these fluid lines 202, 204 needs to compressed at any given time to achieve proportional fluid mixing and desirably linear proportional fluid mixing while the other fluid line remains in an uncompressed or normal state.

Figure 8:
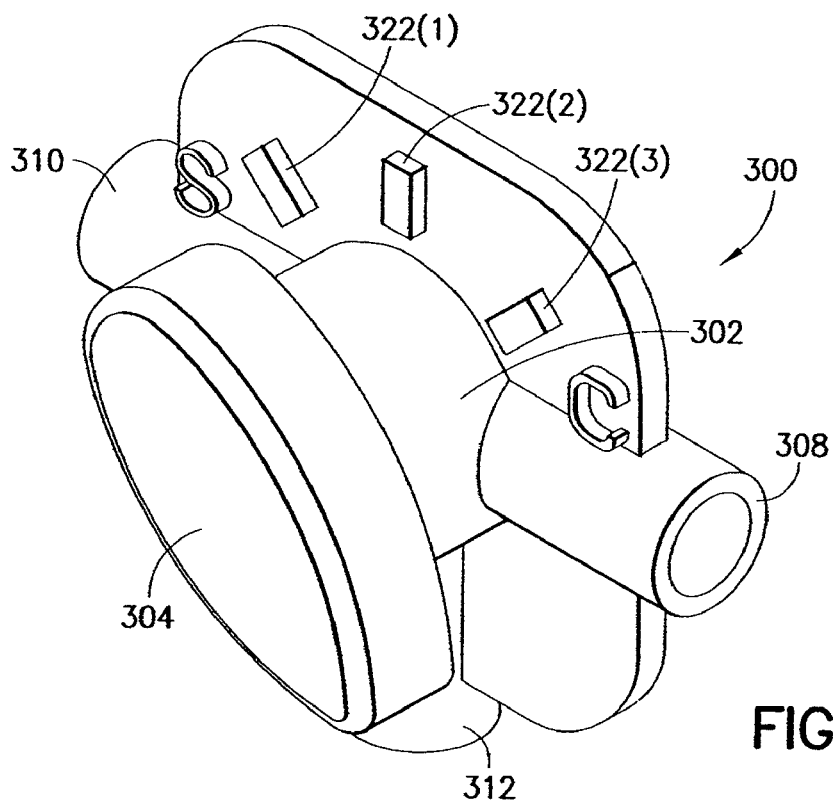
FIG. 8 is a perspective view of an embodiment of a mixing stopcock valve having applications in mixing two (or more) fluids.
Figure 9:
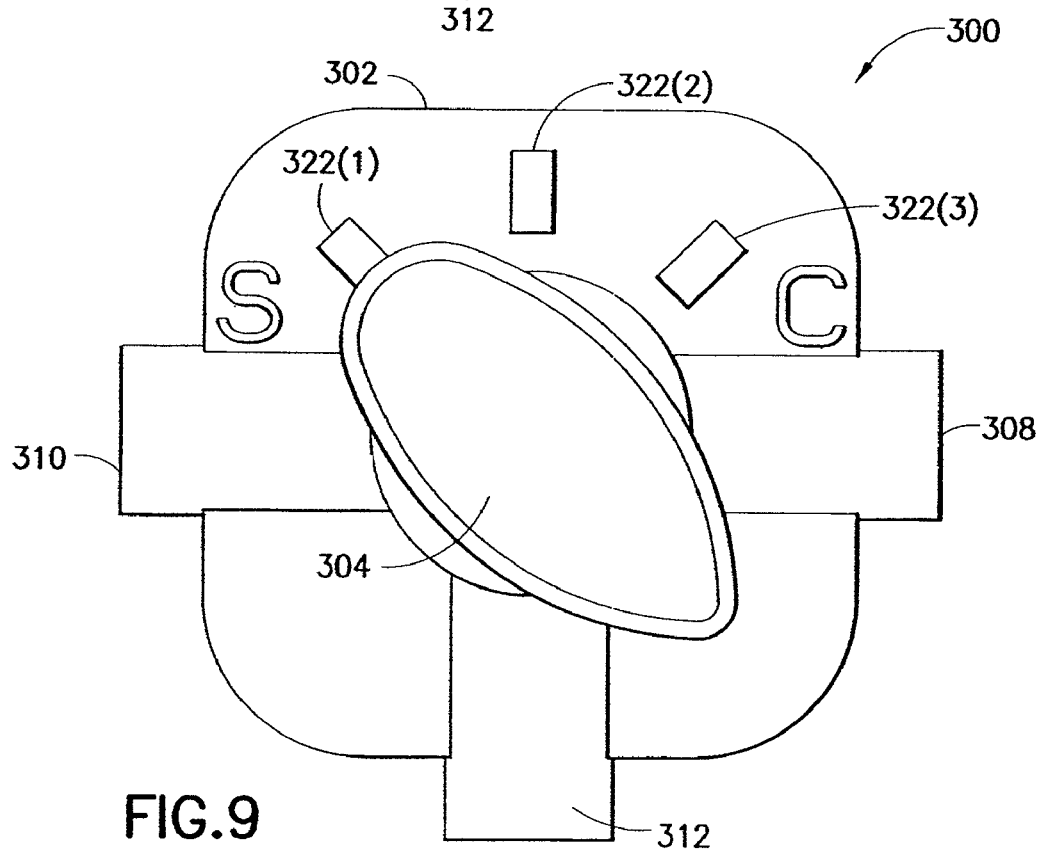
FIG. 9 is a front view of the mixing stopcock of FIG. 8.

Referring to FIGS. 8-10, a "mixing" stopcock valve 300 is illustrated which may be used in the foregoing systems 10, 10a, 100 in the specific locations/applications identified hereinabove. Mixing stopcock valve 300 is adapted to provide proportional mixing of two (and potentially multiple fluids) which have differing upstream pressures and/or viscosities to realize, according to one feature, accurate proportional mixtures of the two fluids. As described previously, mixing-type stopcock valves are generally known, for example, from Fuson et al. However, the mixing-type stopcock valve described in Fuson et al. assumes that upstream pressure and/or viscosity differences are non-existent or minimal between the two or more fluids being mixed in this valve. In the case of contrast media and saline as examples, viscosity of the two fluids differs substantially such that if the Fuson et al. valve were used with contrast and saline, the preset or fixed proportional mixtures, for example, a 50%-50% mixture in one selection position, designed to result from this valve will not occur with any accuracy. The mixing stopcock 300 of FIGS. 8-10 overcomes this limitation with the prior art as differences in upstream pressure and/or viscosity are accounted for in the structure of the valve.

Mixing stopcock valve 300 comprises a stopcock body 302 formed of plastic material, desirably a medical grade plastic material. A stopcock actuator 304 is disposed in a valve chamber 306 defined by stopcock body 302. Additionally, stopcock body 302 defines a plurality of input ports, namely, a contrast input port 308 and a saline input port 310 in the illustrated embodiment. While mixing stopcock valve 300 is described with reference to contrast and saline for illustrative purposes only, it will be clear that mixing stopcock 300 valve is suitable for applications where it is desired to mix any two (or possibly more) fluids of differing upstream pressure and/or viscosity. Stopcock body 302 further defines an outlet port 312. Inlet ports 308, 310 and outlet port 312 may be configured as luer-type connectors as illustrated. Inlet ports 308, 310 comprise contrast and saline inlet ports 308, 310 in the present example.

Stopcock actuator 304 defines a generally T-shaped internal conduit 314. Internal conduit 314 includes a first conduit portion 316 and a second conduit portion 318 of generally similar or equal diameter, and further defines a third conduit portion 320 of reduced diameter relative to the diameters of first and second conduit portions 316, 318. The relative difference in diameters between third conduit portion 320 and first and second portions 316, 318 accounts for upstream pressure and/or viscosity differences between the fluids to be conducted through stopcock valve 300 as in the present case involving contrast and saline. Relative diameter sizing between third conduit portion 320 and first and second portions 316, 318 to account for upstream pressure and/or fluid viscosity differences is readily within the skill of those skilled in the art.

FIG. 10A-10E illustrate operation of mixing stopcock 300 wherein the various positions of stopcock actuator 304 permit full contrast, full saline, or a mixture of contrast and saline to be delivered to outlet port 312. In FIG. 10A, an "off" or no-flow position of stopcock valve 300 is illustrated, wherein stopcock actuator 304 is positioned such that internal conduit 314 is unaligned with inlet ports 308, 310 and outlet port 312 thereby blocking flow into or from internal conduit 314. In FIG. 10B, stopcock actuator 304 is positioned such that first and second conduit portions 316, 318 of internal conduit 314 are aligned with contrast port 308 and outlet port 312, respectively, to permit delivery of contrast only to outlet port 312. In FIG. 10C, stopcock actuator 304 is positioned such that second conduit portion 318 and reduced diameter third conduit portion 320 are aligned are aligned with saline port 310 and outlet port 312, respectively, to permit delivery of saline only to outlet port 312. It is noted that due to the lower viscosity of saline, the reduced diameter third conduit portion 320 permits a similar flow rate of saline to result in outlet port 312 as obtained in the contrast-only setting shown in FIG. 10A. In FIG. 10D, stopcock actuator 304 is positioned such that first conduit portion 316 and reduced diameter third conduit portion 320 are aligned are aligned with saline port 310 and contrast port 308, respectively, to permit delivery of an accurate 50%-50% mixture of saline and contrast to outlet port 312 via second conduit portion 318 of internal conduit 314. In FIG. 10D, by aligning the reduced diameter third conduit portion 320 with contrast port 308 more restriction is present to the high viscosity contrast medium while less restriction is present to the lower viscosity saline passing through saline port 310 and first conduit portion 316. These relative differences in restriction of flow due to diameter differences results in the combining of contrast and saline in an accurate 50%-50% mixture. As shown in FIGS. 8-9, the contrast only setting of FIG. 10B is represented by a "C" tab mark on stopcock body 302, the saline only setting of FIG. 10C is represented by a "S" tab mark on stopcock body 302, and other proportional mixtures between full contrast and full saline are denoted by tab marks 322 on stopcock body 302. For example, tab mark 322(2) corresponds to a 50%-50% mixture of contrast and saline (FIG. 10D), while tab mark 322(1) corresponds to a 75% saline-25% contrast mixture and tab mark 322(3) corresponds to a 75% contrast-25% saline mixture.

FIG. 10E illustrates a further aspect of mixing stopcock 300 wherein a "custom mix" of contrast and saline may be obtained. Gradations representing these custom proportional mixtures may be visually and tactilely provided on the stopcock body 302 by providing a plurality of tab marks similar to tab marks 322 discussed previously between tab mark "S" and tab mark "C" as an example. In FIG. 10E, stopcock actuator 304 is positioned such that first conduit portion 316 is in fluid communication but not aligned directly with saline port 310 resulting in restricted flow of saline, and reduced diameter third conduit portion 320 is in fluid communication but not aligned directly with contrast port 308 resulting in restricted flow of contrast. As such, a specific proportional mixture of contrast and saline is delivered to outlet port 312 when the stopcock actuator 304 is in the orientation shown in FIG. 10E.

As stopcock actuator 304 is rotated clockwise, the flow restriction between third conduit portion 320 and contrast port 308 decreases and, concurrently, the flow restriction between first conduit portion 316 and saline port 310 also decreases. Since the diameter of third conduit portion 320 is less than that of first conduit portion 316, the rate of flow increases faster through third conduit portion 320 than through first conduit portion 316. This result occurs because a larger percentage of third conduit portion 320 comes into increased fluid communication with contrast port 308 more quickly than occurs between first conduit portion 316 and saline port 310 through the same angle of rotation of stopcock actuator 304. Because the flow rate of contrast increases faster and more fluid area is opened to flow more quickly than on the saline "side" as stopcock actuator 304 is rotated clockwise, the concentration of contrast medium flowing through second conduit portion 318 increases with clockwise rotation of the stopcock actuator 304. Once third conduit portion 320 first comes into substantially unrestricted fluid communication with the contrast port 308 (but still less than a direct alignment between third conduit port 320 and contrast port 308 as in FIG. 10D), some flow restriction between first conduit portion 316 and saline port 310 is still present. Thus, maximum concentration of contrast will occur when the third conduit portion 320 first comes into substantially unrestricted fluid communication with contrast port 308. This maximum concentration is greater than 50% because the maximum amount of contrast is able to flow though third conduit portion 320, but first conduit portion 316 is not fully aligned with saline port 310, as in the orientation shown in FIG. 10D, and some flow restriction is still present. As stopcock actuator 304 is rotated further clockwise, the concentration of contrast decreases as the saline flow restriction is removed and more saline is able to flow through first conduit portion 316. Eventually, first conduit portion 316 is fully aligned with saline port 310 as in the orientation shown in FIG. 10D, making the making the mixture flow present in outlet port 312 a 50% contrast/50% saline mixture.

As the stopcock actuator 304 is rotated either clockwise or counterclockwise from the orientation shown in FIG. 10D, the flow of saline will initially decrease as the flow of contrast remains the same. This is again due to the diameter differences between third conduit portion 320 and first conduit portion 316, whereby first conduit portion 316 is almost immediately subject to flow restriction while third conduit portion 320 remains substantially unrestricted. Thus, concentration of contrast will again increase to greater than 50%. Once third conduit portion 320 begins to close as stopcock actuator 304 is continued to be rotated either clockwise or counterclockwise, the rate of flow decreases faster through third conduit portion 320 than through first conduit portion 316 and the concentration of contrast in the mixture again falls. This result is again due to the diameter differences between the third conduit portion 320 and first conduit portion 316. At some point in the rotation of stopcock actuator 304, flow of saline also ceases as the stopcock actuator 304 is placed in the "OFF" position illustrated in FIG. 10A.

The rate at which contrast medium concentration increases with rotation of stopcock actuator 304 depends upon the relative shapes (e.g., diameters) and relative cross-sectional areas of first conduit portion 316 and third conduit portion 320 open to fluid flow. These relative shapes and cross-sections may be sized and configured such that the percentage of contrast medium will vary in a substantially linear proportion to rotation of stopcock actuator 304. In other words, mixing stopcock 300 may be configured such that for a known angle of rotation of stopcock actuator 304, a substantially directly proportional increase or decrease in concentration of contrast medium is obtained in outlet port 312. For example, rotating stopcock actuator 304 of mixing stopcock 300 can cause the concentration of contrast in the fluid mixture in outlet port 312 to range from substantially 0% in the fluid mixture to a percentage greater than 50%, which can be as much as about 80-90% in the fluid mixture. The rate of change in fluid mixture ratio or proportion may be substantially linear or directly proportion between the foregoing minimum and maximum contrast concentrations.

Figure 11:
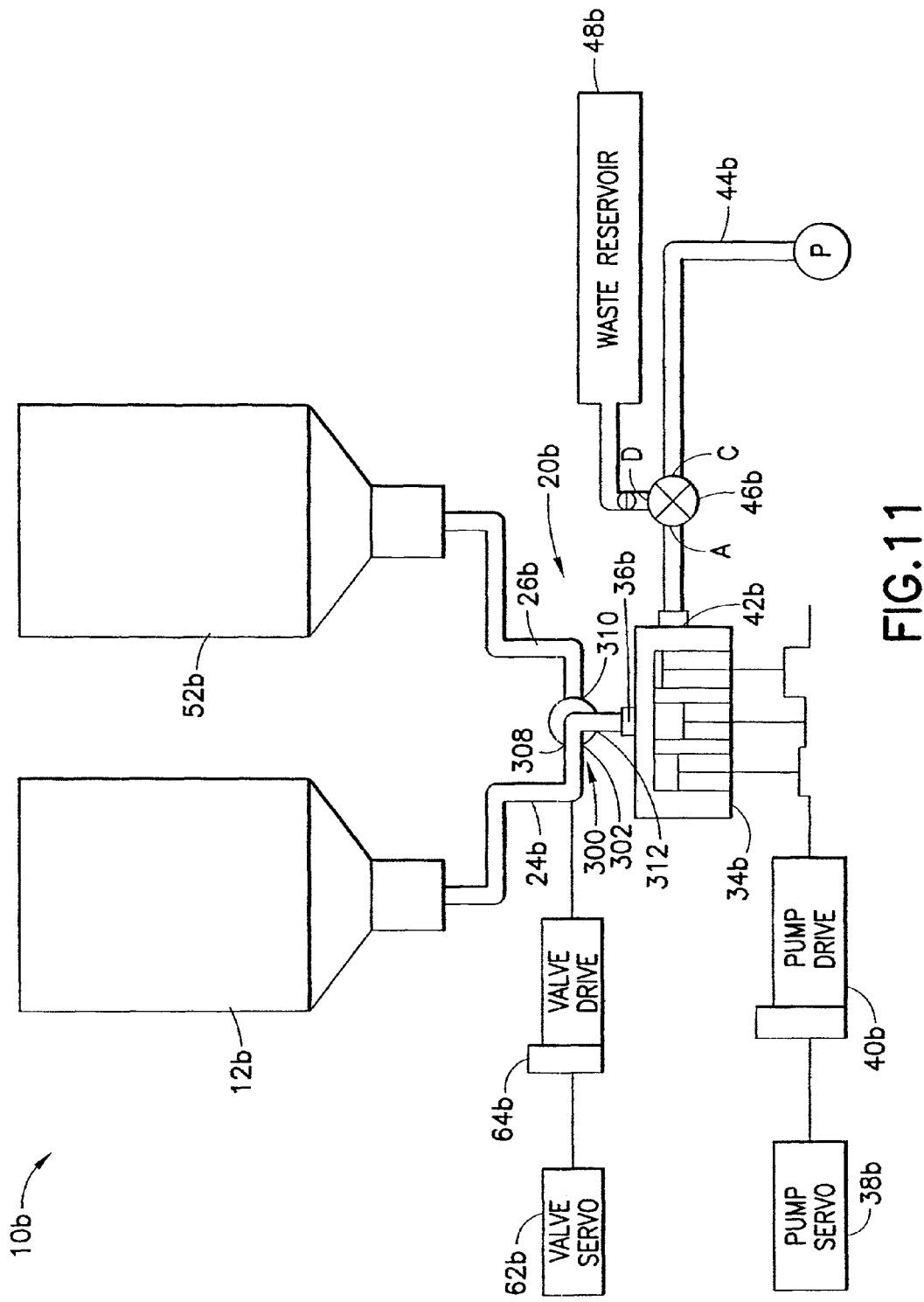
FIG. 11 is a schematic view of a variation of the fluid delivery system of FIG. 2 incorporating a controlled mixing stopcock valve pursuant to FIGS. 8-10.

FIG. 11 illustrates a system 10b which is a variation of system 10a of FIG. 2 and applies the advantages of the "custom mix" application of FIG. 10E to a fluid delivery system comprising two fluids of differing viscosity, such as contrast and saline as an example. The details of system 10b are generally similar to system 10a except that diluent delivery portion 50a is deleted from system 10b and one of contrast containers 12a, 14a, container 14a as an example, is now filled with diluent such as saline and identified in FIG. 11 with reference character 52b for consistency with the foregoing disclosure. Accordingly, fluid path 20b carries both contrast and saline in this embodiment. Additionally, selector valve 22a is replaced with mixing stopcock valve 300, as illustrated, having the features described hereinabove and particularly has the features described in connection with FIG. 10E, namely a "custom mix" capability. Moreover, stopcock valve 300 may be automated in a similar manner to valve 22a. With the positioning of stopcock valve 300 in system 10b, custom proportional mixing, which changes in a substantially linear or directly proportional manner, may be accomplished between contrast medium from container 12b and diluent (e.g., saline) from container 52b which are intended to be exemplary and non-limiting examples of two fluids that may be mixed and delivered by system 10b. Pump 34b may thereby deliver a custom proportional mixture of fluids to patient fluid path 44b via stopcock 46b. A controller 240b similar to controller 240 described previously may be used to control operation of pump 34b via pump servomotor 38b and operation of automatic stopcock valve 300 via valve servomotor 62b. Additionally, controller 240b receives saline flow rate data from flow meter 232b associated with saline fluid path 50b and total flow data via electronic communication with pump servomotor 38b in a similar manner to that described with respect to system 100 discussed hereinabove. As will be clear from the foregoing discussion of controller 240 in system 100, controller 240b provides continuous input to valve servomotor 62b which controls rotational positioning of stopcock actuator 304 to maintain or achieve a desired proportional "custom mix" of contrast and saline to pump inlet 36b. As described previously, flow meter 32b and pump servomotor 38b provide the feedback information or data to controller 240b to allow controller 240b to make continuous rotational updates of stopcock actuator 304 to maintain or achieve the desired proportional "custom mix" of contrast and saline to pump inlet 36b. In other words, controller 240b operates in an analogous manner to controller 240 described previously but in system 10b rotational positional movement of stopcock actuator 304 is used to achieve the desired result of directly proportional or linear changes in contrast concentration to pump inlet 36b of pump 34b over a range of fluid flows.

While embodiments of a system capable of capable of controlled proportional mixing and delivery of fluid mixtures to a patient and, in one particular application, the controlled proportional mixing of contrast medium with saline for delivery to a patient undergoing a medical imaging procedure was provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A system for mixing and delivering fluids, comprising:
   a first fluid source;
   at least a second fluid source;
   a first fluid line in fluid connection with the first fluid source;
   at least a second fluid line in fluid connection with the at least second fluid source;
   a pump having an inlet and an outlet; and
   a mixing stopcock valve having a first input port, at least a second input port, an outlet port, and a stopcock actuator,
   wherein the first input port is in fluid communication with the first fluid line, the at least second input port is in fluid communication with the at least second fluid line, and the outlet port is in fluid communication with an inlet of the pump,
   wherein the stopcock actuator comprises an internal conduit defining a first conduit portion, a second conduit portion, and a third conduit portion of reduced diameter relative to the diameter of the first conduit portion, and
   wherein a positional change in the position of the stopcock actuator provides a change in the fluid mixture ratio of the first and at least second fluids delivered to a patient.

2. The system as claimed in claim 1 wherein the first fluid and the at least second fluid comprise at least contrast media and a diluent.

3. The system as claimed in claim 1 wherein the stopcock actuator is adapted to simultaneously at least partially restrict flow in each of the fluid lines.

4. The system as claimed in claim 1 wherein the pump comprises a positive displacement pump.

5. The system as claimed in claim 4 wherein the positive displacement pump comprises a multi-chamber piston pump.

6. The system as claimed in claim 1 wherein the first fluid line and the at least second fluid line have different diameters.

7. The system as claimed in claim 1 further comprising a flow meter associated with at least one of the fluid lines.

8. The system as claimed in claim 1 wherein the pump comprises a peristaltic pump.

9. A system as claimed in claim 1, further comprising:
   a controller operatively associated with the mixing stopcock valve for controlling positional movement of the stopcock actuator; and
   a flow meter associated with at least one of the fluid lines.

10. The system as claimed in claim 9 wherein the controller effects positional change of the valve actuator at least in part based on feedback from the flow meter.

11. The system as claimed in claim 9 wherein the first fluid and the at least second fluid comprise at least contrast media and a diluent.

12. The system as claimed in claim 9 wherein the stopcock actuator is adapted to simultaneously at least partially restrict flow in each of the fluid lines.

13. The system as claimed in claim 9, further comprising a patient interface device associated with an outlet of the pump.

14. The system as claimed in claim 9 wherein the pump comprises a positive displacement pump.

15. The system as claimed in claim 14 wherein the positive displacement pump comprises a multi-chamber piston pump.

16. The system as claimed in claim 9 wherein the first fluid line and the at least second fluid line have different diameters, or the first input port and the at least second input port have different diameters.

17. The system as claimed in claim 9 wherein the pump comprises a peristaltic pump.

18. A method of mixing and delivering fluids from a first fluid source and at least a second fluid source using a fluid delivery system comprising a pump having an inlet and an outlet, and a mixing stopcock valve having a first input port, at least a second input port, an outlet port and a stopcock actuator comprising an internal conduit defining a first conduit portion, a second conduit portion, and a third conduit portion of reduced diameter relative to the diameter of the first conduit portion, and the method comprising:
   providing a first fluid line with a first end and a second end, and at least a second fluid line with a first end and a second end;
   connecting the first end of the first fluid line to the first fluid source, and the first end of the at least second fluid line to the at least second fluid source;
   connecting the second end of the first fluid line to the first input port of the mixing stopcock valve, and the second end of the at least second fluid line to the at least second input port of the mixing stopcock valve;
   connecting the outlet of the mixing stopcock valve to the inlet of the pump; and
   actuating the stopcock actuator such that a positional change in the position of the stopcock actuator provides a change in the fluid mixture ratio of the first and at least second fluids.

19. The method as claimed in claim 18, further comprising associating a patient interface device with the outlet of the pump.

20. The method as claimed in claim 18 wherein the first fluid line and the at least second fluid line have different diameters.

21. The method as claimed in claim 18 further comprising:
   providing a flow meter associated with at least one of the fluid lines; and
   providing a controller adapted to effect positional change of the stopcock actuator at least in part based on feedback from the flow meter.

* * * * *

UNITED STATES PATENT AND TRADEMARK OFFICE
CERTIFICATE OF CORRECTION

PATENT NO. : 8,162,903 B2  
APPLICATION NO. : 12/848570  
DATED : April 24, 2012  
INVENTOR(S) : Reilly et al.

It is certified that error appears in the above-identified patent and that said Letters Patent is hereby corrected as shown below:

IN THE SPECIFICATION

In Column 6, Line 15, delete "DESCRIPTION" and insert -- DETAILED DESCRIPTION --, therefor.

IN THE CLAIMS

In Claim 1, Column 17, Lines 7-8, delete "a first fluid source; at least a second fluid source;" and insert -- a first fluid source configured to supply a first fluid; at least a second fluid source configured to supply at least a second fluid; --, therefor.

In Claim 2, Column 17, Line 28, delete "claim 1" and insert -- claim 1, --, therefor.

In Claim 3, Column 17, Line 31, delete "claim 1" and insert -- claim 1, --, therefor.

In Claim 4, Column 17, Line 34, delete "claim 1" and insert -- claim 1, --, therefor.

In Claim 5, Column 17, Line 36, delete "claim 4" and insert -- claim 4, --, therefor.

In Claim 6, Column 17, Line 38, delete "claim 1" and insert -- claim 1, --, therefor.

In Claim 6, Column 17, Lines 38-39, delete "the first fluid line and the at least second fluid line have different diameters" and insert -- the first fluid line has a first diameter, the at least second fluid line has an at least second diameter, and the first diameter differs from the at least second diameter --, therefor.

In Claim 7, Column 17, Line 40, delete "claim 1" and insert -- claim 1, --, therefor.

In Claim 8, Column 17, Line 42, delete "claim 1" and insert -- claim 1, --, therefor.

Signed and Sealed this  
Fifth Day of February, 2013

Teresa Stanek Rea  
*Acting Director of the United States Patent and Trademark Office*

CERTIFICATE OF CORRECTION (continued)
U.S. Pat. No. 8,162,903 B2

IN THE CLAIMS

In Claim 10, Column 17, Line 49, delete "claim 9" and insert -- claim 9, --, therefor.

In Claim 11, Column 17, Line 52, delete "claim 9" and insert -- claim 9, --, therefor.

In Claim 12, Column 18, Line 1, delete "claim 9" and insert -- claim 9, --, therefor.

In Claim 13, Column 18, Line 4, delete "claim 9" and insert -- claim 9, --, therefor.

In Claim 13, Column 18, Line 5, delete "associated with an outlet of the pump" and insert -- associated with the outlet of the pump --, therefor.

In Claim 14, Column 18, Line 6, delete "claim 9" and insert -- claim 9, --, therefor.

In Claim 15, Column 18, Line 8, delete "claim 14" and insert -- claim 14, --, therefor.

In Claim 16, Column 18, Line 10, delete "claim 9" and insert -- claim 9, --, therefor.

In Claim 16, Column 18, Lines 10-13, delete "the first fluid line and the at least second fluid line have different diameters, or the first input port and the at least second input port have different diameters" and insert -- the first fluid line has a first diameter, the at least second fluid line has an at least second diameter, and the first diameter differs from the at least second diameter, or the first input port has a first port diameter, the at least second input port has an at least second port diameter, and the first port diameter differs from the at least second port diameter --, therefor.

In Claim 17, Column 18, Line 14, delete "claim 9" and insert -- claim 9, --, therefor.

In Claim 18, Column 18, Lines 23-24, delete "the first conduit portion, and the method comprising" and insert -- the first conduit portion, the method comprising --, therefor.

In Claim 18, Column 18, Lines 40-41, delete "ratio of the first and at least second fluids." and insert -- ratio of a first fluid and at least a second fluid. --, therefor.

In Claim 20, Column 18, Line 44, delete "claim 18" and insert -- claim 18, --, therefor.

In Claim 20, Column 18, Lines 44-46, delete "the first fluid line and the at least second fluid line have different diameters" and insert -- the first fluid line has a first diameter, the at least second fluid line has an at least second diameter, and the first diameter differs from the at least second diameter --, therefor.

In Claim 21, Column 18, Line 47, delete "claim 18" and insert -- claim 18, --, therefor.